(12) United States Patent
Ballantyne et al.

(10) Patent No.: US 7,588,921 B1
(45) Date of Patent: Sep. 15, 2009

(54) MESSENGER RNA PROFILING: BODY FLUID IDENTIFICATION USING MULTIPLEX REAL TIME-POLYMERASE CHAIN REACTION (Q-PCR)

(75) Inventors: John Ballantyne, Orlando, FL (US); Jane Juusola, Glen Allen, VA (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 313 days.

(21) Appl. No.: 11/232,277

(22) Filed: Sep. 21, 2005

Related U.S. Application Data

(60) Provisional application No. 60/612,057, filed on Sep. 22, 2004.

(51) Int. Cl.
*C12P 19/34* (2006.01)
*C07H 21/04* (2006.01)

(52) U.S. Cl. ..................................... 435/91.2; 536/24.3

(58) Field of Classification Search ........................ None
See application file for complete search history.

(56) References Cited

U.S. PATENT DOCUMENTS

| | | | |
|---|---|---|---|
| 7,270,983 B1 * | 9/2007 | Ballantyne et al. | 435/91.2 |
| 2002/0169730 A1 * | 11/2002 | Lazaridis | 706/20 |
| 2004/0259105 A1 * | 12/2004 | Fan et al. | 435/6 |
| 2006/0024791 A1 * | 2/2006 | Kozlowski et al. | 435/69.1 |

OTHER PUBLICATIONS

Crawford et al. The biological importance of measuring individual variation. The Journal of Experimental Biology, 210(9):1613-21, 2007.*
Boorman et al. Variation in the hepatic gene expression in individual male Fischer rats. Toxicologic Pathology, 33:102-110, 2005.*
Alberts, Bruce, et al. *Molecular Biology of the Cell*, 4th ed., (2002). Chapter II. Section 7. "The Molecular Genetic Mechanisms That Create Specialized Cell Types." http://www.ncbi.nlm.nih.gov./entrez/query.fcgi?cmd=Search&db=books&doptcmdl=Genbo....
Bauer, M., et al. *International Journal of Legal Medicine*. vol. 117 pp. 175-179. (2003). "Protamine mRNA as Molecular Marker for Spermatozoa in Seman Stains."
Bauer, M., et al. *Journal of Forensic Science*. vol. 47. No. 6. pp. 1278-1282. (2002). "Evaluation of mRNA Markers for the Identification of Menstrual Blood". http://www.astm.org.
Juusola, Jane, et al. *Forensic Science International*. vol. 135. pp. 85-96. (2003). "Messenger RNA profiling: A Prototype Method to Supplant Conventional Methods for Body Fluid Identification."
Juusola, Jane, et al. *American Academy of Forensic Science (AAFS) Presentation*, Feb. 2002 "The D3evelopment of an RNA Based Assay System to Supplant Conventional Methods for Body Fluid Identification."

* cited by examiner

*Primary Examiner*—Young J Kim
*Assistant Examiner*—Samuel Woolwine
(74) *Attorney, Agent, or Firm*—Brian S. Steinberger; Frances Olmsted; Law Offices of Brian S. Steinberger, P.A.

(57) ABSTRACT

This invention relates to a ribonucleic acid (RNA) based assay system for body fluid identification, and in particular to a novel, multiplex, parallel assay system based on messenger RNA expressed in human tissue, and to a method for using the same.

6 Claims, 2 Drawing Sheets

| Body Fluid | Gene | Primer and Probe Sequences/dyes |
|---|---|---|
| Housekeeping Gene | GAPDH | F: 5'- ATG GAA ATC CCA TCA CCA TCT T (Seq ID 1)<br>R: 5'- CGC CCC ACT TGA TTT TGG (Seq ID 2)<br>P: 5'-NED- CAG GAG CGA GAT CC (Seq ID 3) |
| | GNAS | F: 5'- TGA ACG CCG CAA GTG GAT (Seq ID 4)<br>R: 5'- GGC GGT TGG TCT GGT TGT C (Seq ID 5)<br>P: 5'-NED- CTT CAA CGA TGT GAC TGC (Seq ID 6) |
| Blood | ALAS2 | F: 5'- GCC GAC ACC CTC AGG TCT T (Seq ID 7)<br>R: 5'- GAA ACT TAC TGG TGC CTG AGA TGT T (Seq ID 8)<br>P: 5'-VIC- AAG CCA CAC AGG AGA C (Seq ID 9) |
| | SPTB | F: 5'- GCC TTT AAT GCC CTG ATA CAC AA (Seq ID 10)<br>R: 5'- GAG TCC TTC AGC TTA TCA AAG TCG AT (Seq ID 11)<br>P: 5'- FAM- CAC CGG CCC GAC CT (Seq ID 12) |
| Saliva | HTN3 | F: 5'- CTT GGC TCT CAT GCT TTC CAT (Seq ID 13)<br>R: 5'- TTT ATA CCC ATG ATG TCT CTT TGC A (Seq ID 14)<br>P: 5'-FAM- ACT GGA GCT GAT TCA C (Seq ID 15) |
| | STATH | F: 5'- TCT TGG CTC TCA TGG TTT CCA (Seq ID 16)<br>R: 5'- CCA ATT CTA CGC AAA AAT TTC TCT T (Seq ID 17)<br>P: 5'-VIC- ATT GGA GCT GAT TCA TC (Seq ID 18) |
| Semen | PRM1 | F: 5'- CAG ATA TTA CCG CCA GAG ACA AAG (Seq ID 19)<br>R: 5'- AAT TAG TGT CTT CTA CAT CTC GGT CTG T (Seq ID 20)<br>P: 5'-FAM- CAG CAC CTC ATG GCT (Seq ID 21) |
| | PRM2 | F: 5'- GGC GCA AAA GAC GCT CC (Seq ID 22)<br>R: 5'- GCC CAG GAA GCT TAG TGC C (Seq ID 23)<br>P: 5'-VIC- TTC TGC AGC CTC TGC GAT (Seq ID 24) |
| Menstrual Blood | MMP-7 | F: 5'- GGG AGG CAT GAG TGA GCT ACA (Seq ID 25)<br>R: 5'- TGG CAT TTT TTG TTT CTG AGT CAT A (Seq ID 26)<br>P: 5'-FAM- AAC AGG CTC AGG ACT AT (Seq ID 27) |
| | MMP-10 | F: 5'- TGG TCA CTT CAG CTC CTT TCC T (Seq ID 28)<br>R: 5'- AAT GGC AGA ATC AAC AGC ATC TC (Seq ID 29)<br>P: 5'-VIC- CAC CTT ACA TAC AGG ATT G (Seq ID 30) |

F=forward primer, R=reverse primer, P=probe

Figure 1

| Real-time PCR primer and probe for body fluid identification triplexes | | | | | | | | |
|---|---|---|---|---|---|---|---|---|
| | Blood Triplex 1 | Blood Triplex 2 | Saliva Triplex 1 | Saliva Triplex 2 | Semen Triplex 1 | Semen Triplex 2 | Menstrual Blood Triplex 1 | Menstrual Blood Triplex 2 |
| SPTB F<br>SPTB R<br>SPTB-FAM | 900 nM<br>900 nM<br>200 nM | 900 nM<br>900 nM<br>250 nM | - | - | - | - | - | - |
| ALAS F<br>ALAS R<br>ALAS-VIC | 900 nM<br>900 nM<br>250 nM | 900 nM<br>900 nM<br>250 nM | - | - | - | - | - | - |
| HTN3 F<br>HTN3 R<br>HTN3-FAM | - | - | 900 nM<br>900 nM<br>250 nM | 900 nM<br>900 nM<br>200 nM | - | - | - | - |
| STATH F<br>STATH R<br>STATH-VIC | - | - | 900 nM<br>900 nM<br>250 nM | 900 nM<br>900 nM<br>250 nM | - | - | - | - |
| PRM1 F<br>PRM1 R<br>PRM1-FAM | - | - | - | - | 900 nM<br>900 nM<br>250 nM | 900 nM<br>900 nM<br>250 nM | - | - |
| PRM2 F<br>PRM2 R<br>PRM2-VIC | - | - | - | - | 900 nM<br>900 nM<br>250 nM | 900 nM<br>900 nM<br>250 nM | - | - |
| MMP-7 F<br>MMP-7 R<br>MMP7-FAM | - | - | - | - | - | - | 900 nM<br>900 nM<br>250 nM | 900 nM<br>900 nM<br>200 nM |
| MMP10 F<br>MMP10 R<br>MMP10-VIC | - | - | - | - | - | - | 900 nM<br>900 nM<br>250 nM | 900 nM<br>900 nM<br>250 nM |
| GAPDH F<br>GAPDH R<br>GAPDH-NED | 300 nM<br>300 nM<br>75 nM | - | 600 nM<br>600 nM<br>150 nM | - | 900 nM<br>900 nM<br>250 nM | - | 150 nM<br>150 nM<br>75 nM | - |
| GNAS F<br>GNAS R<br>GNAS-NED | - | 900 nM<br>900 nM<br>250 nM | - | 900 nM<br>900 nM<br>250 nM | - | 1200 nM<br>1200 nM<br>300 nM | - | 300 nM<br>300 nM<br>150 nM |

Figure 2

SEQUENCE LISTING

<160> NUMBER OF SEQ ID NOS: 30

<210> SEQ ID NO 1
<211> LENGTH: 16
<212> TYPE: DNA
<213> ORGANISM: homo sapiens
<220> FEATURE:
<221> NAME/KEY: misc_feature
<222> LOCATION: (1)..(1)
<223> OTHER INFORMATION: n is a, c, g, t or u

<400> SEQUENCE: 1
ndcaggagcg agatcc                                              16

<210> SEQ ID NO 2
<211> LENGTH: 22
<212> TYPE: DNA
<213> ORGANISM: homo sapiens

<400> SEQUENCE: 2
atggaaatcc catcaccatc tt                                       22

<210> SEQ ID NO 3
<211> LENGTH: 18
<212> TYPE: DNA
<213> ORGANISM: homo sapiens

<400> SEQUENCE: 3
cgccccactt gattttgg                                            18

<210> SEQ ID NO 4

```
<211> LENGTH: 18
<212> TYPE: DNA
<213> ORGANISM: homo sapiens

<400> SEQUENCE: 4
tgaacgccgc aagtggat                                                 18

<210> SEQ ID NO 5
<211> LENGTH: 19
<212> TYPE: DNA
<213> ORGANISM: homo sapiens

<400> SEQUENCE: 5
ggcggttggt ctggttgtc                                                19

<210> SEQ ID NO 6
<211> LENGTH: 20
<212> TYPE: DNA
<213> ORGANISM: homo sapiens
<220> FEATURE:
<221> NAME/KEY: misc_feature
<222> LOCATION: (1)..(1)
<223> OTHER INFORMATION: n is a, c, g, t or u

<400> SEQUENCE: 6
ndcttcaacg atgtgactgc                                               20

<210> SEQ ID NO 7
<211> LENGTH: 19
<212> TYPE: DNA
<213> ORGANISM: homo sapiens

<400> SEQUENCE: 7
gccgacaccc tcaggtctt                                                19

<210> SEQ ID NO 8
<211> LENGTH: 25
<212> TYPE: DNA
<213> ORGANISM: homo sapiens

<400> SEQUENCE: 8
gaaacttact ggtgcctgag atgtt                                         25

<210> SEQ ID NO 9
<211> LENGTH: 18
<212> TYPE: DNA
<213> ORGANISM: homo sapiens

<400> SEQUENCE: 9
vcaagccaca caggagac                                                 18

<210> SEQ ID NO 10
<211> LENGTH: 23
<212> TYPE: DNA
<213> ORGANISM: homo sapiens

<400> SEQUENCE: 10
gcctttaatg ccctgataca caa                                           23

<210> SEQ ID NO 11
<211> LENGTH: 26
<212> TYPE: DNA
<213> ORGANISM: homo sapiens

<400> SEQUENCE: 11
```

-continued

```
gagtccttca gcttatcaaa gtcgat                                    26

<210> SEQ ID NO 12
<211> LENGTH: 14
<212> TYPE: DNA
<213> ORGANISM: homo sapiens

<400> SEQUENCE: 12
caccggcccg acct                                                 14

<210> SEQ ID NO 13
<211> LENGTH: 21
<212> TYPE: DNA
<213> ORGANISM: homo sapiens

<400> SEQUENCE: 13
cttggctctc atgctttcca t                                         21

<210> SEQ ID NO 14
<211> LENGTH: 25
<212> TYPE: DNA
<213> ORGANISM: homo sapiens

<400> SEQUENCE: 14
tttataccca tgatgtctct ttgca                                     25

<210> SEQ ID NO 15
<211> LENGTH: 16
<212> TYPE: DNA
<213> ORGANISM: homo sapiens

<400> SEQUENCE: 15
actggagctg attcac                                               16

<210> SEQ ID NO 16
<211> LENGTH: 21
<212> TYPE: DNA
<213> ORGANISM: homo sapiens

<400> SEQUENCE: 16
tcttggctct catggtttcc a                                         21

<210> SEQ ID NO 17
<211> LENGTH: 25
<212> TYPE: DNA
<213> ORGANISM: homo sapiens

<400> SEQUENCE: 17
ccaattctac gcaaaaattt ctctt                                     25

<210> SEQ ID NO 18
<211> LENGTH: 17
<212> TYPE: DNA
<213> ORGANISM: homo sapiens

<400> SEQUENCE: 18
attggagctg attcatc                                              17

<210> SEQ ID NO 19
<211> LENGTH: 24
<212> TYPE: DNA
<213> ORGANISM: homo sapiens
```

```
<400> SEQUENCE: 19
cagatattac cgccagagac aaag                                          24

<210> SEQ ID NO 20
<211> LENGTH: 28
<212> TYPE: DNA
<213> ORGANISM: homo sapiens

<400> SEQUENCE: 20
aattagtgtc ttctacattc tggtctgt                                      28

<210> SEQ ID NO 21
<211> LENGTH: 15
<212> TYPE: DNA
<213> ORGANISM: homo sapiens

<400> SEQUENCE: 21
cagcacctca tggct                                                    15

<210> SEQ ID NO 22
<211> LENGTH: 17
<212> TYPE: DNA
<213> ORGANISM: homo sapiens

<400> SEQUENCE: 22
ggcgcaaaag acgctcc                                                  17

<210> SEQ ID NO 23
<211> LENGTH: 19
<212> TYPE: DNA
<213> ORGANISM: homo sapiens

<400> SEQUENCE: 23
gcccaggaag cttagtgcc                                                19

<210> SEQ ID NO 24
<211> LENGTH: 20
<212> TYPE: DNA
<213> ORGANISM: homo sapiens

<400> SEQUENCE: 24
vcttctgcag cctctgcgat                                               20

<210> SEQ ID NO 25
<211> LENGTH: 21
<212> TYPE: DNA
<213> ORGANISM: homo sapiens

<400> SEQUENCE: 25
gggaggcatg agtgagctac a                                             21

<210> SEQ ID NO 26
<211> LENGTH: 25
<212> TYPE: DNA
<213> ORGANISM: homo sapiens

<400> SEQUENCE: 26
tggcattttt tgtttctgag tcata                                         25

<210> SEQ ID NO 27
<211> LENGTH: 17
<212> TYPE: DNA
<213> ORGANISM: homo sapiens
```

```
<400> SEQUENCE: 27
aacaggctca ggactat                                                17

<210> SEQ ID NO 28
<211> LENGTH: 22
<212> TYPE: DNA
<213> ORGANISM: homo sapiens

<400> SEQUENCE: 28
tggtcacttc agctcctttc ct                                          22

<210> SEQ ID NO 29
<211> LENGTH: 23
<212> TYPE: DNA
<213> ORGANISM: homo sapiens

<400> SEQUENCE: 29
aatggcagaa tcaacagcat ctc                                         23

<210> SEQ ID NO 30
<211> LENGTH: 21
<212> TYPE: DNA
<213> ORGANISM: homo sapiens

<400> SEQUENCE: 30
vccaccttac atacaggatt g                                           21
```

MESSENGER RNA PROFILING: BODY FLUID IDENTIFICATION USING MULTIPLEX REAL TIME-POLYMERASE CHAIN REACTION (Q-PCR)

This invention claims the benefit of priority from U.S. Provisional Application Ser. No. 60/612,057 filed Sep. 22, 2004 the content of which is incorporated herein by reference.

FIELD OF THE INVENTION

This invention relates to a ribonucleic acid (RNA) based assay system for body fluid identification, and in particular to a novel, multiplex, parallel assay system based on messenger RNA expressed in human tissue, and to a method for using the same.

SEQUENCE LISTING

Appendix A is a sequence listing of DNA sequences identified in FIG. 1; the content of Appendix A is also submitted on a compact disc and is incorporated herein by reference. Attached hereto is one compact disc containing the following files:

SEQ. 1 Housekeeping gene GAPDH (Seq. ID 1)
SEQ. 2 Housekeeping gene GAPDH (Seq. ID 2)
SEQ. 3 Housekeeping gene GAPDH (Seq. ID 3)
SEQ. 4 Housekeeping gene GNAS (Seq. ID 4)
SEQ. 5 Housekeeping gene GNAS (Seq. ID 5)
SEQ. 6 Housekeeping gene GNAS (Seq. ID 6)
SEQ. 7 Blood ALAS2 (Seq. ID 7)
SEQ. 8 Blood ALAS2 (Seq. ID 8)
SEQ. 9 Blood ALAS2 (Seq. ID 9)
SEQ. 10 Blood SPTB (Seq. ID 10)
SEQ. 11 Blood SPTB (Seq. ID 11)
SEQ. 12 Blood SPTB (Seq. ID 12)
SEQ. 13 Saliva HTN3 (Seq. ID 13)
SEQ. 14 Saliva HTN3 (Seq. ID 14)
SEQ. 15 Saliva HTN3 (Seq. ID 15)
SEQ. 16 Saliva STATH (Seq. ID 16)
SEQ. 17 Saliva STATH (Seq. ID 17)
SEQ. 18 Saliva STATH (Seq. ID 18)
SEQ. 19 Semen PRM1 (Seq. ID 19)
SEQ. 20 Semen PRM1 (Seq. ID 20)
SEQ. 21 Semen PRM1 (Seq. ID 21)
SEQ. 22 Semen PRM2 (Seq. ID 22)
SEQ. 23 Semen PRM2 (Seq. ID 23)
SEQ. 24 Semen PRM2 (Seq. ID 24)
SEQ. 25 Menstrual Blood MMP-7 (Seq. ID 25)
SEQ. 26 Menstrual Blood MMP-7 (Seq. ID 26)
SEQ. 27 Menstrual Blood MMP-7 (Seq. ID 27)
SEQ. 28 Menstrual Blood MMP-10 (Seq. ID 28)
SEQ. 29 Menstrual Blood MMP-10 (Seq. ID 29)
SEQ. 30 Menstrual Blood MMP-10 (Seq. ID 30)

BACKGROUND AND PRIOR ART

Conventional methods of body fluid identification use a variety of labor-intensive, technologically diverse techniques that are performed in a series, not parallel, manner and are costly in terms of time and consumption of sample. It used to be standard practice to perform biochemical, serological, and immunological tests to identify the body fluid(s) comprising a biological stain. Increasingly, however, classical methods for body fluid identification have no confirmatory technique for some frequently encountered body fluids. For example, there is no definitive test for the presence of saliva or vaginal secretions, and urine identification can be problematic. The need exists for a more reliable, efficient assay system to supplant conventional methods for body fluid identification.

Previous research in the development of a ribonucleic acid (RNA) based assay system for the identification of body fluids, included considerations for the use of protein and messenger RNA (mRNA) since both are expressed in a tissue-type specific manner. However, multiplex analysis of complex protein mixtures, such as those present in body fluid stains, requires further developments in the field of proteomics. Whereas, messenger RNA (mRNA), the molecular intermediate between genetic deoxyribonucleic acid (DNA) and expressed protein, is, at present, supported by technologies for massively parallel analysis in the field of genomics.

As reported by B. Alberts, et al. *Molecular Biology of the Cell* $3^{rd}$ ed., Garland Publishing Inc., NY, 1994, a pattern of gene expression is produced that is unique to each cell type and is evinced by the presence, as well as, the relative abundance of specific mRNAs. Each cell type, such as, blood monocytes, lymphocytes, ejaculated spermatozoa, epithelial cells lining the oral cavity or epidermal cells, has a unique pattern of gene expression.

Specific gene expression patterns for saliva were reported by J. Juusola and J. Ballantyne in February 2002 in a presentation to the American Academy of Forensic Science (AAFS) entitled, "The Development of an RNA Based Assay System for Body Fluid Identification," and in *Forensic Science International*, Vol. 135 (2003) pages 85-96 ("Messenger RNA Profiling: a Prototype Method to Supplant Conventional Methods for Body Fluid Identification"). Semen specific genes were reported by J. Juusola and J. Ballantyne in "The Development of an RNA Based Assay System for Body Fluid Identification," presented to AAFS, February 2002. M. Bauer and D. Patzelt also identified semen specific genes in an article, "Protamine mRNA as Molecular Marker for Spermatozoa in Semen Stains," *International Journal of Legal Medicine* Vol. 117 (2003) pages 175-179. Additionally, M. Bauer and D. Patzelt identified menstrual blood specific genes in an article, "Evaluation of mRNA markers for the identification of menstrual blood," *Jl. Forensic Science* Vol. 47 (6) November (2002) pages 1278-1282.

As more and more tissue-specific genes (mRNAs) are identified for use in the positive identification of body fluids and tissues of forensic importance, there is an increasing need for a device or assay system that provides simultaneous and semi-automated analysis through a common assay format. The novel, multiplex, parallel assay system of the present invention provides a common assay format and offers many advantages over the conventional analysis procedures for body fluid identification.

SUMMARY OF THE INVENTION

A primary objective of the present invention is to provide facile identification of the tissue components present in a body fluid stain.

A second objective of the present invention is to supplant the battery of serological and biochemical tests currently employed in the forensic serology laboratory.

A third objective of the present invention is to provide a common assay format that -provides greater specificity in the identification of body fluids with improved timeliness.

A fourth objective of the present invention is to decrease sample consumption during analysis of stains containing body fluids.

A fifth objective of the present invention is to provide simultaneous and semi-automated analysis through a common assay format.

A sixth objective of the present invention is to provide a multiplex analysis of body fluids in an assay format that is compatible with DNA analysis methodologies.

A preferred method for identifying the presence or absence of at least four body fluids from a human being in a single or mixed stain, includes obtaining a sample stain consisting of a body fluid from a human being, extracting total ribonucleic acid (RNA) from the sample stain, treating the total RNA with an enzyme, initiating a reverse-transcriptase (RT) reaction by treating total RNA with random decamers to produce cDNA, amplifying the cDNA using body fluid specific genes (BFG)-specific unlabeled primers and the corresponding labeled probe, identifying the body fluid by determining the values of a house keeping gene (HSK) and the value of the BFG, and then subtracting the value of the BFG from the value of the HSK gene, wherein a positive value for both BFGs would indicate the presence of the BFG in the bodily fluid. The more preferred method for identifying the presence or absence of at least four body fluids from a human being in a single or mixed stain, further includes extracting the total RNA with a denaturing solution. The preferred extracting solution is guanidine isothiocyanate-phenol:chloroform and the extracted total RNA is precipitated with an organic solvent, which is preferably isopropanol.

The preferred enzyme used to treat the extracted total RNA is deoxyribonuclease I (DNase I).

It is preferred that the method of the present invention include four body fluids selected from the group consisting of one or more of blood, saliva, semen and menstrual blood, wherein portions of two BFG's identifying one particular body fluid and one HSK gene are present, providing a triplex assay.

It is more preferred that the probes fluoresce and the values are determined by finding the cycle threshold (Ct) of the HSK and each of the BFG and then subtracting the Ct of the BFG from the Ct of the HSK and the HSK is selected from at least one of GAPDH or GNAS.

Preferably, the BFG is one or more of the group consisting of ALAS2, SPTB, STATH, HTN3, PRM1, PRM2, MMP-7, and MMP-10.

A preferred kit for use in identifying the presence or absence of a bodily fluid, comprising BFG and HSK specific primers and probes is provided. More preferably the BFG specific primers are constructed from one or more of the group consisting of the ALAS2, SPTB, STATH, HTN3, PRM1, PRM2, MMP-7, and MMP-10 genes. The preferred housekeeping gene is selected from at least one of GAPDH and GNAS.

Preferably, the primers for the preferred kit, are one or more sequences selected from the group consisting of 5'-atg-gaa-atc-cca-tca-cca-tct-t (Seq ID 1), 5'-cgc-ccc-act-tga-tt-tgg (Seq ID 2), 5'-tga-acg-ccg-caa-gtg-gat (Seq ID 4), 5'-ggc-ggt-tgg-tct-ggt-tgt-c (Seq ID 5), 5'-gcc-gac-acc-ctc-agg-tct-t (Seq ID 7), 5'-gaa-act-tac-tgg-tgc-ctg-aga-tgt-t (Seq ID 8), 5'-gcc-ttt-aat-gcc-ctg-ata-cac-aa (Seq ID 10), 5'-gag-tcc-ttc-agc-tta-tca-aag-tcg-at (Seq ID 11), 5'-ctt-ggc-tct-cat-gct-ttc-cat (Seq ID 13), 5'-ttt-ata-ccc-atg-atg-tct-ctt-tgc-a (Seq ID 14), 5'-tct-tgg-ctc-tca-tgg-ttt-cca (Seq ID 16), 5'-cca-att-cta-cgc-aaa-aat-ttc-tct-t (Seq ID 17), 5'-cag-ata-tta-ccg-cca-gag-aca-aag (Seq ID 19), 5'-aat-tag-tgt-ctt-cta-cat-ctc-ggt-ctg-t (Seq ID 20), 5'-ggc-gca-aaa-gac-gct-cc (Seq ID 22), 5'-gcc-cag-gaa-gct-tag-tgc-c (Seq ID 23), 5'-ggg-agg-cat-gag-tga-gct-aca (Seq ID 25), 5'-tgg-cat-ttt-ttg-ttt-ctg-agt-cat-a (Seq ID 26), 5'-tgg-tca-ctt-cag-ctc-ctt-tcc-t (Seq ID 0.28), 5'-aat-ggc-aga-atc-aac-agc-atc-tc (Seq ID 29).

The preferred primers for identifying the source of body fluids comprising one or more of the group consisting of (ALAS2 primers) 5'-gcc-gac-acc-ctc-agg-tct-t (Seq ID 7), 5'-gaa-act-tac-tgg-tgc-ctg-aga-tgt-t (Seq ID 8), (SPTB primers) 5'-gcc-ttt-aat-gcc-ctg-ata-cac-aa (Seq ID 10), 5'-gag-tcc-ttc-agc-tta-tca-aag-tcg-at (Seq ID 11), (HTN3 primers) 5'-ctt-ggc-tct-cat-gct-ttc-cat (Seq ID 13), 5'-ttt-ata-ccc-atg-atg-tct-ctt-tgc-a (Seq ID 14), (STATH primers) 5'-tct-tgg-ctc-tca-tgg-ttt-cca (Seq ID 16), 5'-cca-att-cta-cgc-aaa-aat-ttc-tct-t (Seq ID 17), (PRM1 primers) 5'-cag-ata-tta-ccg-cca-gag-aca-aag (Seq ID 19), 5'-aat-tag-tgt-ctt-cta-cat-ctc-ggt-ctg-t (Seq ID 20), (PRM2 primers) 5'-ggc-gca-aaa-gac-gct-cc (Seq ID 22), 5'-gcc-cag-gaa-gct-tag-tgc-c (Seq ID 23), (MMP-7 primers) 5'-ggg-agg-cat-gag-tga-gct-aca (Seq ID 25), 5'-tgg-cat-ttt-ttg-ttt-ctg-agt-cat-a (Seq ID 26), (MMP-10 primers) 5'-tgg-tca-ctt-cag-ctc-ctt-tcc-t (Seq ID 28), 5'-aat-ggc-aga-atc-aac-agc-atc-tc (Seq ID 29).

The preferred primers for said housekeeping gene comprising one or more of the group consisting of (GAPDH primers) 5'-atg-gaa-atc-cca-tca-cca-tct-t (Seq ID 1), 5'-cgc-ccc-act-tga-tt-tgg (Seq ID 2), (GNAS primers) 5'-tga-acg-ccg-caa-gtg-gat (Seq ID 4), 5'-ggc-ggt-tgg-tct-ggt-tgt-c (Seq ID 5).

The preferred probes for the kit of the present invention, are labeled with fluorescent dyes and the probes are one or more sequences selected from the group consisting of 5'-cag-gag-cga-gat-cc (Seq ID 3), 5'-ctt-caa-cga-tgt-gac-tgc (Seq ID 6), 5'-aag-cca-cac-agg-aga-c (Seq ID 9), 5'-cac-cgg-ccc-gac-ct (Seq ID 12), 5'-act-gga-gct-gat-tca-c (Seq ID 15), 5'-att-gga-gct-gat-tca-tc (Seq ID 18), 5'-cag-cac-ctc-atg-gct (Seq ID 21), 5'-ttc-tgc-agc-ctc-tgc-gat (Seq ID 24), 5'-aac-agg-ctc-agg-act-at (Seq ID 27), 5'-cac-ctt-aca-tac-agg-att-g (Seq ID 30).

The preferred probes for identifying the source of body fluids comprising one or more of the group consisting of (ALAS2 probe) 5'-aag-cca-cac-agg-aga-c (Seq ID 9), (SPTB probe) 5'-cac-cgg-ccc-gac-ct (Seq ID 12), (HTN3 probe) 5'-act-gga-gct-gat-tca-c (Seq ID 15), (STATH probe) 5'-att-gga-gct-gat-tca-tc (Seq ID 18), (PRM1 probe) 5'-cag-cac-ctc-atg-gct (Seq ID 21), (PRM2 probe) 5'-ttc-tgc-agc-ctc-tgc-gat (Seq ID 24),(MMP-7 probe) 5'-aac-agg-ctc-agg-act-at (Seq ID 27), (MMP-10 probe) 5'-cac-ctt-aca-tac-agg-att-g (Seq ID 30); more preferably the kit uses probes wherein ALAS2 probe 5'-aag-cca-cac-agg-aga-c (Seq ID 9) is labeled with VIC, SPTB probe 5'-cac-cgg-ccc-gac-ct (Seq ID 12) is labeled with FAM, HTN3 probe 5'-act-gga-gct-gat-tca-c (Seq ID 15) is labeled with FAM, STATH probe 5'-att-gga-gct-gat-tca-tc (Seq ID 18) is labeled with VIC, PRM1 probe 5'-cag-cac-ctc-atg-gct (Seq ID 21) is labeled with FAM, PRM2 probe 5'-ttc-tgc-agc-ctc-tgc-gat (Seq ID 24) is labeled with VIC, MMP-7 probe 5'-aac-agg-ctc-agg-act-at (Seq ID 27) is labeled with FAM, MMP-10 probe 5'-cac-ctt-aca-tac-agg-att-g (Seq ID 30) is labeled with VIC.

The preferred probes for said housekeeping genes comprising one or more of the group consisting of (GAPDH probe) 5'-cag-gag-cga-gat-cc (Seq ID 3), (GNAS probe) 5'-ctt-caa-cga-tgt-gac-tgc (Seq ID 6); more preferably the invention uses probes, wherein GAPDH probe 5'-cag-gag-cga-gat-cc (Seq ID 3) is labeled with NED, GNAS probe 5'-ctt-caa-cga-tgt-gac-tgc (Seq ID 6) is labeled with NED.

Further objectives and advantages of this invention will be apparent from the following detailed description and example of a presently preferred embodiment.

BRIEF DESCRIPTION OF THE DRAWING

FIG. 1 shows the DNA sequences of the PCR primers for the various body fluid-specific genes and housekeeping genes used in the assay.

FIG. 2 shows the optimum DNA primer and probe concentrations for each gene in each triplex.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The invention provides a multiplex, parallel assay to identify the tissue source for at least four body fluids from a human being. The first step in the development of the invention has been the identification of tissue-specific genes that are expressed in only one tissue. For example, each tissue type is comprised of cells that have a unique transcriptome, or gene expression profile, also known as the messenger ribonucleic acid (mRNA) profile. The collection of genes that are expressed within the constellation of differentiated cells that make up a body fluid is called the multicellular transcriptome. These genes comprise ubiquitously expressed housekeeping (HSK) genes such as GAPDH and GNAS, which are responsible for cell maintenance functions, and genes that are specifically expressed in certain tissues only. The mRNA molecules are present in different quantities depending on the particular species of mRNA and the cell type, and can be classified as abundant, moderately abundant and rare. Although the present invention is dependent on the identification of tissue-specific mRNA molecules, it is not to be considered a limitation of the invention. As previously discussed, tissue-specific genes are still in the process of being identified.

The present invention provides a body fluid identification system containing real time PCR triplexes that are able to recognize each of the candidate genes.

An example of some of the body fluid-specific genes for each of four body fluids that are the subject of the present invention, are identified in the table below:

| BODY FLUID-SPECIFIC GENE: | BODY FLUIDS | | | |
|---|---|---|---|---|
| Delta-aminolevulinate synthase 2 (erythoid) (ALAS2) | BLOOD | | | |
| Beta-spectrin (SPTB) | BLOOD | | | |
| Statherin (STATH) | | SALIVA | | |
| Histatin 3 (HTN3) | | SALIVA | | |
| Protamine 1 (PRM1) | | | SEMEN | |
| Protamine 2 (PRM2) | | | SEMEN | |
| Matrix metalloproteinase 7 (MMP-7) | | | | MENSTRUAL BLOOD |
| Matrix metalloproteinase 10 (MMP-10) | | | | MENSTRUAL BLOOD |

Gene-specific unlabeled forward and reverse primers along with fluorescent dye-labeled probes for any two genes identified above and a housekeeping gene, are incorporated into a single, triplexed real-time polymerase chain reaction (qPCR). During amplification, the fluorescent dye from the gene-specific probe is released and produces a fluorescent signal that is detected by the real-time PCR instrument. The resulting fluorescence signals identify the body fluids that are present in the sample as a single or mixed stain. For this invention, the body fluids include, but are not limited to, blood, saliva, semen or menstrual blood The following example provides further explanation of the present invention.

EXAMPLE

A physiological stain is prepared by collecting human blood via venipuncture; collecting 50 microliter (μl) aliquots placed onto cotton gauze and dried at room temperature. Freshly ejaculated semen is collected in plastic cups, and allowed to dry onto cotton swabs at room temperature. Buccal scrapings and saliva samples were obtained on cotton swabs, and dried at room temperature. Vaginal secretions, such as menstrual blood, are also obtained and dried at room temperature. For RNA or DNA isolation a 50 microliter (μl) bloodstain or a single semen, menstrual blood or saliva stained cotton swab is used.

For RNA isolation, total RNA is extracted from blood, saliva, vaginal secretions and semen stains with a denaturing solution, such as, guanidine isothiocyanate-phenol:chloroform and precipitated with isopropanol. Next, the extracted total RNA is treated with an enzyme, deoxyribonuclease I (DNase I), and then reverse-transcribed using random decamers as the first strand primer, producing complementary DNA (cDNA). Finally, the cDNA is amplified using gene-specific primers.

Based on the above extraction and separation techniques, a multiplex reverse-transcription polymerase chain reaction (RT-PCR) assay is developed for the definitive identification of all of the body fluids commonly encountered in forensic casework analysis, namely blood, saliva, semen, and menstrual blood. The triplexes are composed of two body fluid-specific genes and a housekeeping (HSK) gene, GAPDH (glyceraldehyde-3-phospate dehydrogenase) or GNAS (guanine nucleotide binding protein, alpha stimulating) or others, and have been optimized for the detection of blood, saliva, semen, and menstrual blood as single or mixed stains. The methodology is based on gene expression profiling analysis in which the body fluid-specific genes are identified by detecting the presence of appropriate mRNA species. Gene-specific unlabeled primers and the corresponding probe labeled with a fluorescent dye, such as VIC, FAM or NED, are incorporated into a single multiplexed real-time polymerase chain reaction (qPCR). VIC, FAM and NED are commercially available, trademarked fluorescent dyes.

The primers and probes are custom synthesized commercially according to our specifications. Invitrogen Corporation (Carlsbad, Calif.) synthesized the primers and the labeled probes are from Applied Biosystems (Foster City, Calif.). The unique primer and probe sequences are shown in FIG. 1. For the body fluid identification triplexes, optimal primer and probe concentrations were determined experimentally and are as follows: For the blood triplex (SPTB/ALAS2/GAPDH), the primer concentrations were 900/900/300 nM, respectively, and the probe concentrations were 250/250/75 nM, respectively. For the blood triplex (SPTB/ALAS2/GNAS), the primer concentrations were 900 nM for each primer and the probe concentrations were 250 nM for each probe. For the saliva triplex (HTN3/STATH/GAPDH), the primer concentrations were 900/900/600 nM, respectively, and the probe concentrations were 250/250/150 nM, respectively. For the saliva triplex (HTN3/STATH/GNAS), the primer concentrations were 900 nM for each primer, and the probe concentrations were 200/250/250 nM for each probe. In the semen triplex (PRM1/PRM2/GAPDH), the optimal primer concentration was 900 nM for each gene, and the probe concentration was 250 nM for each gene. For the semen triplex (PRM1/PRM2/GNAS), the optimal primer concentrations were 900/900/1200 nM, and the probe concentrations were 250/250/300 nM, respectively. For the menstrual blood triplex (MMP-7/MMP-11/GAPDH), the primer concentrations were 900/900/150 nM, respectively, and the probe concentrations were 250/250/75 nM, respectively. For the menstrual blood triplex (MMP-7/MMP-11/GNAS), the primer concentrations were 900/900/300 nM, respectively, and the probe concentrations were 200/250/150 nM, respectively. These optimal primer and probe concentrations are also listed in FIG. 2, however, these concentrations should not limit the invention as other concentrations will also be functional.

As the polymerase chain reaction (PCR) product is amplified, the gene-specific probe is cleaved and the fluorescent dye is released producing a fluorescence signal that is detected by the real-time PCR instrument. The resulting fluorescence signals identify the body fluids that are present in the sample as a single or mixed stain. The resulting fluorescence signal and corresponding Ct value can be used to identify those body fluids present by determining the delta Ct (dCt) values generated using the cycle threshold (Ct) of the housekeeping gene (HSK) and the Ct of each of the body fluid specific genes (BFG), (Ct HSK-Ct BFG). Ct is the cycle number at which the fluorescent signal passes a pre-determined threshold. Depending on the body fluid-specific genes (BFGs) being tested, two positive dCt values would indicate the presence of a particular body fluid, while two negative dCt values would indicate the absence of that body fluid. Whereas, one positive dCt and one negative dCt would indicate the possible presence of that body fluid and suggest the need for additional testing of the sample. However, this approach is not limited to utilizing fluorescence as a detection method, as other detection methods may be used. Also, data analysis is not limited to utilizing the calculations described above, as other methods of calculation may be used.

Advantages of the mRNA-based approach, compared to conventional biochemical analysis include, but are not limited to, greater specificity, simultaneous and semi-automated analysis through a common assay format, improved timeliness, decreased sample consumption and compatibility with DNA extraction methodologies.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for identifying the presence of one or more body fluids from a human being in a single or mixed stain the fluids selected from the group consisting of non-menstrual blood, menstrual blood, saliva and semen, comprising the steps of:
   a) obtaining a sample stain comprising a body fluid from a human being;
   b) extracting total ribonucleic acid (RNA) from the sample stain;
   c) treating the total RNA from step b) with an enzyme
   d) initiating a reverse-transcriptase (RT) reaction by treating the total RNA from step c) with random decamers to produce cDNA;
   e) amplifying a pair of body-fluid specific genes (BFGs) selected from the pairs: ALAS2 and SPTB, specific for non-menstrual blood, HTN3 and STATH, specific for saliva, PRM1 and PRM2, specific for semen, and MMP-7 and MMP-10, specific for menstrual blood, wherein said amplifying utilizes two primers and a probe for each BFG;
   f) amplifying a housekeeping gene (HSK) selected from one of GAPDH and GNAS, wherein said amplifying utilizes two primers and a probe for each HSK;
   g) determining the presence of the body fluid in the stain by measuring the cycle threshold (Ct) value of the house keeping gene (HSK) and the Ct values of both BFGs, and then subtracting the Ct value of each BFG from the Ct value of the HSK gene, wherein a positive dCt (HSK-Ct minus BFG-Ct) value of each BFG indicates the presence of the corresponding body fluid in the stain.

2. The method of claim 1, wherein the total RNA is extracted with a denaturing solution.

3. The method of claim 2, wherein the extracting solution is guanidine isothiocyanate-phenol:chloroform.

4. The method of claim 3, wherein the extracted total RNA is precipitated with an organic solvent.

5. The method of claim 4, wherein the organic solvent is isopropanol.

6. The method of claim 1, wherein the enzyme used to treat the extracted total RNA is deoxyribonuclease I (DNase I).

* * * * *

UNITED STATES PATENT AND TRADEMARK OFFICE
CERTIFICATE OF CORRECTION

| | | |
|---|---|---|
| PATENT NO. | : 7,588,921 B1 | Page 1 of 1 |
| APPLICATION NO. | : 11/232277 | |
| DATED | : September 15, 2009 | |
| INVENTOR(S) | : John Ballantyne et al. | |

It is certified that error appears in the above-identified patent and that said Letters Patent is hereby corrected as shown below:

Col. 1, line 16, insert:

-- STATEMENT REGARDING FEDERALLY SPONSORED RESEARCH OR DEVELOPMENT

This subject invention was made with government support under the Federal Bureau of Investigation, federal contract number JFB103287. The government has certain rights in this invention. --

Signed and Sealed this
Eighth Day of March, 2011

David J. Kappos
*Director of the United States Patent and Trademark Office*